United States Patent
Bologna et al.

(10) Patent No.: US 11,596,601 B2
(45) Date of Patent: Mar. 7, 2023

(54) MUCOADHESIVE GEL COMPOSITION

(71) Applicant: Viramal Ltd., London (GB)

(72) Inventors: William Bologna, New York, NY (US);
François Boutignon, Clermont-Ferrand (FR); Lea Louvel, Villons-les-Buissons (FR); Finn Larsen, Hawick (GB); Simona Fiore, London (GB); Oliver Bates, London (GB)

(73) Assignee: Viramal Limited, London (GB)

( * ) Notice: Subject to any disclaimer, the term of this patent is extended or adjusted under 35 U.S.C. 154(b) by 312 days.

(21) Appl. No.: 16/663,759

(22) Filed: Oct. 25, 2019

(65) Prior Publication Data

US 2020/0129422 A1    Apr. 30, 2020

Related U.S. Application Data

(60) Provisional application No. 62/751,475, filed on Oct. 26, 2018.

(51) Int. Cl.
| | |
|---|---|
| *A61K 9/00* | (2006.01) |
| *A61K 9/06* | (2006.01) |
| *A61K 31/57* | (2006.01) |
| *A61K 47/06* | (2006.01) |
| *A61K 47/14* | (2017.01) |
| *A61K 47/32* | (2006.01) |
| *A61K 47/38* | (2006.01) |

(52) U.S. Cl.
CPC ............. *A61K 9/006* (2013.01); *A61K 9/06* (2013.01); *A61K 31/57* (2013.01); *A61K 47/06* (2013.01); *A61K 47/14* (2013.01); *A61K 47/32* (2013.01); *A61K 47/38* (2013.01)

(58) Field of Classification Search
CPC ........ A61K 9/006; A61K 31/57; A61K 47/06; A61K 47/14; A61K 47/38
See application file for complete search history.

(56) References Cited

U.S. PATENT DOCUMENTS

| | | |
|---|---|---|
| 4,767,751 A | 8/1988 | Davis |
| 5,849,019 A | 12/1998 | Yoon |

(Continued)

FOREIGN PATENT DOCUMENTS

| | | |
|---|---|---|
| CA | 3068157 A1 | 12/2018 |
| DE | 102015207621 A1 | 10/2016 |

(Continued)

OTHER PUBLICATIONS

Anonymous, Natural Testosterone; Testosteroids [online]; 2014; downloaded from URL<https://web.archive.org/web/20150114212448/http://www.testosteroids.com/Natural-testosterone>Nov. 21, 2017; 4 pages.

(Continued)

*Primary Examiner* — San Ming R Hui
(74) *Attorney, Agent, or Firm* — Greenberg Traurig, LLP

(57) ABSTRACT

A pharmaceutical mucoadhesive gel composition for delivering therapeutic agents (such as progesterone) by buccal, nasal, vaginal and rectal administration, thereby avoiding the hepatic first-pass metabolism. The gel composition comprises a vehicle with a gel-forming agent and a bioadhesive agent; and a therapeutic agent dispersed or suspended in the vehicle.

19 Claims, 4 Drawing Sheets

(56) References Cited

U.S. PATENT DOCUMENTS

| | | | |
|---|---|---|---|
| 6,187,323 | B1 | 2/2001 | Aiache |
| 6,198,323 | B1 | 3/2001 | Offord |
| 6,579,865 | B2 | 6/2003 | Mak |
| 6,872,382 | B1 | 3/2005 | Gamache |
| 6,967,023 | B1 | 11/2005 | Eini |
| 6,994,863 | B2 | 2/2006 | Eini |
| 7,105,184 | B2 | 9/2006 | Pauly |
| 7,368,122 | B1 | 5/2008 | Dow |
| 8,536,380 | B2 | 9/2013 | Scheffler |
| 8,877,230 | B2 * | 11/2014 | Mattern .............. A61P 15/00 424/434 |
| 8,940,354 | B2 | 1/2015 | Marangoni |
| 9,180,091 | B2 | 11/2015 | Bernick |
| 9,248,136 | B2 | 2/2016 | Bernick |
| 9,289,382 | B2 | 3/2016 | Bernick |
| 2003/0180352 | A1 | 9/2003 | Patel |
| 2004/0143026 | A1 | 7/2004 | Shah |
| 2006/0240111 | A1 | 10/2006 | Fernández |
| 2006/0269485 | A1 | 11/2006 | Friedman |
| 2007/0110812 | A1 | 5/2007 | Xia |
| 2007/0148195 | A1 | 6/2007 | Ebert |
| 2008/0039398 | A1 | 2/2008 | Ousler |
| 2010/0137198 | A1 | 6/2010 | Eini |
| 2011/0158920 | A1 | 6/2011 | Morley |
| 2011/0195036 | A1 | 8/2011 | Clemente |
| 2012/0301464 | A1 | 11/2012 | Friedman |
| 2014/0161889 | A1 | 6/2014 | Mikulásik |
| 2014/0186278 | A1 | 7/2014 | Franke |
| 2014/0349981 | A1 * | 11/2014 | Evers ................ A61K 31/573 514/171 |
| 2015/0004213 | A1 | 1/2015 | Ron |
| 2015/0283066 | A1 | 10/2015 | Katz |

FOREIGN PATENT DOCUMENTS

| | | | | |
|---|---|---|---|---|
| EP | 0793996 | A1 | 9/1997 | |
| EP | 0861657 | A2 | 9/1998 | |
| EP | 3641821 | A2 | 4/2020 | |
| GB | 2581876 | A | 2/2020 | |
| JP | 11512732 | A | 11/1999 | |
| JP | 2007528864 | A | 10/2007 | |
| JP | 2010514748 | A | 5/2010 | |
| JP | 2013540698 | A | 11/2013 | |
| JP | 2020524690 | A | 8/2020 | |
| WO | 9320799 | A1 | 10/1993 | |
| WO | 9712618 | A1 | 4/1997 | |
| WO | 9962497 | A1 | 12/1999 | |
| WO | 0000120 | A1 | 1/2000 | |
| WO | 2008081175 | A2 | 7/2008 | |
| WO | 2008089405 | A1 | 7/2008 | |
| WO | 2012019991 | A1 | 2/2012 | |
| WO | 2012156820 | A1 | 11/2012 | |
| WO | 2014004018 | A1 | 1/2014 | |
| WO | WO-2014004018 | A1 * | 1/2014 | ............ A21D 2/165 |
| WO | 2014026707 | A1 | 2/2014 | |
| WO | 2014193667 | A1 | 12/2014 | |
| WO | 2015/187840 | | 12/2015 | |
| WO | 2017120492 | A1 | 7/2017 | |

OTHER PUBLICATIONS

BalanceDocs [online]; 2016; downloaded from <URL http://balancedocs.com/article-library-n-z/testosterone-supplementation/> on Oct. 26, 2018; 4 pages. (Year: 2016).

New Dictionary of Traditional Chinese Medicine, Wang Benxiang, Tianjin Science and Technology Press, pp. 840 published on May 31, 1996 (English translation).

PCT/EP2019/082893 International Search Report and Written Opinion dated Mar. 4, 2021.

PCT/US2017/012564 International Search Report and Written Opinion dated Apr. 18, 2017.

Singh et al., Preparation and characterization of novel carbopol based bigels for topical delivery of metronidazole for the treatment of bacterial vaginosis. Materials Science and Engineering C. vol. 44. pp. 151-158. Aug. 5, 2014.

Wu et al., "Determination of danazol in human plasma by liquid chromatogram-mass spectrometry", Clin Pharm J, 2005, vol. 40, No. 10, 3 pages.

Zhu, Zhaolu, et al. "The development of polycarbophil as a bio adhesive material in pharmacy." Asian Journal of Pharmaceutical Sciences, vol. 8, No. 4 (2013), p. 218-227. Jan. 8, 2013.

Nahoul, "Profiles of plasma estrogens, progesterone and their metabolites after oral or vaginal administration of estradiol or progesterone" *Maturitas* 1993; 16:185-202.

Simon, "The absorption of oral micronized progesterone: the effect of food, dose proportionality, and comparison with intramuscular progesterone" *Fertility & Sterility* 1993; 60(1):26-33.

Germond, "Comparison of the efficacy and safety of two formulations of micronized progesterone (Ellios™ and Utrogestan™) used as luteal phase support after in vitro fertilization" *Fertility & Sterility* 2002; 77(2):313-317.

Boddupalli, "Mucoadhesive drug delivery system: An overview" *J Adv Pharm Technol Res*. 2010; 1(4):381-387.

Shaikh, "Mucoadhesive drug delivery systems" *J Pharm Bioallied Sci*. 2011;3(1):89-100.

Peppas, "Hydrogels as mucoadhesive and bioadhesive materials: a review" *Biomaterials* 1996; 17(16): 1553-1561.

Sudhakar, "Buccal bioadhesive drug delivery—A promising option for orally less efficient drugs" *Journal of Controlled Release* 2006; 114:15-40.

Russo, "A focus on mucoadhesive polymers and their application in buccal dosage forms" *Journal of Drug Delivery Science & Technology* 2016; 32: 113-125.

Kumar, "Denture Adhesives in Prosthodontics: An Overview" *J Int Oral Health* 2015;7(Suppl 1):93-5.

Drug Label (Physician Information) for Crinone 4% and Crinone 8% (progesterone gel), Jun. 2017.

Fanchin, "Transvaginal Administration of Progesterone" *Obstetrics & Gynecology* 1997; 90(3):396-401.

Progesterone Dosage Guide from Drugs.Com website, printed Oct. 7, 2018.

Drug Label for Striant (testosterone buccal system), Nov. 2009.

Search Report by the European Patent Office dated Jan. 8, 2020 for application PCT/IB2019/059105.

Written Opinion by the European Patent Office dated Jan. 8, 2020 for application PCT/IB2019/059105.

\* cited by examiner

MUCOADHESIVE GEL COMPOSITION

TECHNICAL FIELD

This invention relates to a bioadhesive formulation, more particular to pharmaceuticals formulated for buccal, nasal, vaginal, or rectal administration.

BACKGROUND

There is a constant need for providing methods for safe and effective administration of physiologically active ingredients. Oral administration is one administration regime that is commonly used because of its relatively simple regime. However, numerous drugs are problematic for oral delivery due to their low solubility and susceptibility to first pass metabolism in the liver. For such drugs, alternative ports of entry are of interest, and since the mucosal tissue is readily accessible and has a large surface area, mucoadhesive drug delivery systems has been the subject of much research and product development.

Drug delivery via the mucosal tissue has advantages such as overcoming the drawbacks of conventional administration routes, for instance, the direct entry of the drug into the systemic circulation obviates the first pass hepatic effect. In addition, mucosal drug delivery is generally noninvasive, thereby avoiding the uncomfortable aspects of intravenous, intramuscular, or subcutaneous delivery means. Furthermore, active substance can be easily administered and if necessary, removed from application site. Thus mucosal drug delivery system is therefore of value in delivering a growing number of drugs.

Mucoadhesive drug delivery systems are known in the art and include in situ formed hydrogels, pastes, tablets, and films. However, these known mucoadhesive drug delivery systems primarily utilize water soluble/aqueous carrier vehicles, and said system therefore has the disadvantage that natural bodily fluids have a tendency to clear applied formulations from the site of administration. For example, in the mouth, saliva, natural replacement of the mucosal tissue, eating, drinking, and speaking movements are some of the problems that have limited the effectiveness and residence time of buccal mucoadhesive drug delivery systems.

Accordingly, the known products lack one or several of the preferred characteristics for an efficient and commercially acceptable drug delivery device. Some characteristics which are preferred by users of bioadhesive carriers include controlled water-erodability, ease of handling and application to the delivery/treatment site, and ease of comfort, with minimal foreign body sensation. Other preferred characteristics for an effective and user-friendly product for administration to mucosal surfaces include instantaneous adhesion to mucosal surface upon application; and increased residence time for delivering the pharmaceutical component and/or for enhanced absorption.

Thus, there remains a demand for improved bioadhesive formulations capable of overcoming the challenges known in the art.

SUMMARY

Thus, it is a first aspect of the present invention to provide a mucoadhesive gel composition that can provide a systemic delivery of an active ingredient for a prolong period of time and with increased bioavailability, and wherein said gel is not formed in situ.

It is a second aspect of the present invention to provide a mucoadhesive gel composition arranged for providing sustained delivery of an active ingredient in a substantially zero order release profile.

It is a third aspect of the present invention to provide a mucoadhesive gel composition that is substantially free and preferably completely free of volatile agents, surfactants and/or substances known to cause mucosal irritation.

It is a forth aspect of the present invention to provide an applicator for administration of the mucoadhesive gel composition, which is easy to use and ensures that the required amount of gel composition is applied to the administration site.

These and further aspects are achieved according to the present invention by providing a mucoadhesive gel composition, comprising:
  a vehicle comprising a gel-forming agent and a bioadhesive agent, and wherein said gel-forming agent constituting 0.5-30% by weight of the gel composition; and
  the bioadhesive agent constituting 1-40% by weight of the gel composition; and
  a therapeutic agent constituting 1-20% by weight of the gel composition, and wherein said therapeutic agent is dispersed or suspended in the vehicle.

It is known that adhesion of compositions onto mucous tissue can be impaired by the mucociliary clearance system, a natural defense mechanism of the body against the deposition of impurities onto the mucous membrane, and that said clearance may remove the applied composition before the required amount of drug/therapeutic agent has been delivered. Since the mucoadhesive gel composition according to the invention comprises a bioadhesive, said gel composition will remain at the site of application, thereby prolonging the residence time at the absorption site. This, will ensure that the required/sufficient amount of therapeutic agent is delivered at the administration site, and accordingly provide a decrease in drug administration frequency and an increase in patient compliance.

The mucoadhesive gel composition is designed to be applied to the buccal, nasal, vaginal, and rectal mucosa with direct transmucosal absorption into the systemic circulation, thereby avoiding the hepatic first-pass metabolism.

The site of administration depends on the therapeutic agent. For instance, progesterone, which is an endogenous steroid sex hormone that plays a crucial part in the menstrual cycle and maintenance of pregnancy, may preferably be applied via the buccal mucosa.

In addition to progesterone's natural role as a hormone, progesterone is also used as a medication. Progesterone is sometimes called the "hormone of pregnancy" because it has many roles in the preparation and maintenance of pregnancy. Among them, progesterone converts the endometrium to its secretory stage to prepare the uterus for implantation. But high systemic levels of progesterone are required for transformation of the endometrium to the secretory stage, which is crucial to infertility treatments in which the endometrium is prepared for embryo implantation. High systemic levels of progesterone are also required for the treatment of estrogen receptor/progesterone receptor "double positive" breast cancer.

The conventional routes of delivery for progesterone administration are by oral ingestion, intramuscular (IM) injection, and vaginal gel application. One of the major problems with oral administration of progesterone is the rapid and extensive metabolism it undergoes on its first pass through the liver. More than 90% of orally-administered progesterone is metabolized in its first pass through the liver, and as a result, its half-life in serum is only about 5 minutes. Thus, for medical conditions requiring treatment with high, sustained blood levels of progesterone, sufficient therapeutic levels cannot be achieved through oral administration. Moreover, the progesterone metabolites can cause adverse side-effects such as dizziness and drowsiness.

Progesterone by IM injection is an effective alternative. However, this route has lower patient acceptance because the injections may be painful. Vaginal gel formulations of progesterone are available for topical administration into the vagina. However, this route of administration achieves only low plasma levels, and the therapeutic efficacy on the endometrium is actually the result of localized, direct vagina-to-uterus transit. See Fanchin et al, "Transvaginal Administration of Progesterone" (1997) Obstetrics & Gynecology 90(3):396-401. Thus, the vaginal gel formulation is not effective in conditions that require treatment with sustained high levels of progesterone in the systemic circulation.

In a similar manner, other therapeutic agents may or will have an optimal administration route.

In another aspect, the invention is a pharmaceutical product comprising a single-use disposable applicator. Contained in the disposable applicator is the mucoadhesive pharmaceutical gel composition of the invention. The amount of therapeutic agent provided in the disposable applicator can vary depending on its concentration in the gel composition and the amount of gel composition contained in the disposable applicator. In some embodiments, the disposable applicator contains 30-150 mg of the therapeutic agent and is arranged for delivering a volume of the mucoadhesive gel composition between 0.4-1.5 grams depending on the administration site. In some embodiments, the disposable applicator is provided as part of a package of multiple identical disposable applicators. The number of disposable applicators in the package can vary depending on the intended duration and frequency of use. In some embodiments, each of the applicator packages contains 15-60 disposable applicators.

In another aspect, the invention is a pharmaceutical product comprising a metered-dose dispenser for dispensing the gel-composition i.e. a semi-solid material (e.g. as opposed to a metered-dose inhaler for aerosolized medications). Contained in the metered-dose dispenser is the pharmaceutical gel composition of the invention. The amount of therapeutic agent provided in the metered-dose dispenser will vary depending on its concentration in the gel composition, the amount of gel composition contained in the dispenser, and its intended duration and frequency of use. In some embodiments, the metered-dose dispenser contains between 5 and 100 grams of gel composition according to the invention and wherein said composition respectively contains between 500 mg-8 grams of the therapeutic agent.

The amount of therapeutic agent provided by each activation of the metered-dose dispenser will vary depending on its concentration in the gel composition and the amount of gel composition dispensed with each activation. In some embodiments, each activation of the metered-dose dispenser dispenses at least 0.3 grams of the pharmaceutical gel composition; and in some cases, 0.4-1.5 grams. In some embodiments, each dosages of the gel compositions comprises 30-150 mg of the therapeutic agent.

In another aspect, the invention is a method of inducing secretory transformation of the endometrium in a female patient. The method comprises applying the pharmaceutical gel composition of the invention onto a desired mucosa, e.g. the buccal mucosal or sublingual site in the patient's oral cavity and adhering it thereto. The therapeutic agent is delivered directly to the systemic circulation by transmucosal absorption, thereby avoiding first-pass metabolism through the liver. This results in sufficiently high levels of the therapeutic agent in the systemic circulation. In some embodiments, the method achieves an amount of therapeutic agent in the plasma or serum of at least 5 ng/mL; in some cases, at least 8 ng/mL; in some cases, at least 11 ng/mL; and in some cases, at least 15 ng/mL. This high level of therapeutic agent may be sustained for a sufficient duration of time for therapeutic effectiveness. In some cases, this high level of therapeutic agent is sustained for at least 6 hours duration after dosing; and in some cases, at least 12 hours duration after dosing.

The invention may also be considered as a method of administering a therapeutic agent to a patient by buccal delivery, or a method of treating a medical condition. A variety of different types of medical conditions could be treated by the invention, as further explained below.

DETAILED DESCRIPTION

Figure 1:
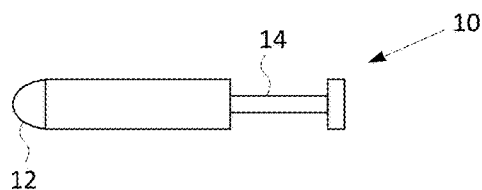
FIG. 1 shows an example of a single-use disposable applicator filled with a gel composition of the invention.

The pharmaceutical gel composition comprises a vehicle comprising a gel-forming agent, a bioadhesive agent, and a therapeutic agent dispersed in the vehicle. As used herein, amounts expressed in weight percentages are relative to the total weight of the gel composition (w/w).

Vehicle.

Within the context of the present invention, the term "vehicle" refers to the formulation which "carries" the therapeutic agent also named the active pharmaceutical ingredient—API. Within the context of the present invention, the vehicle comprises both the gel-forming agent and the bioadhesive agent.

The choice of vehicle will depend upon the nature of the API and the mucosal site of treatment. For instance, hydrophilic API's have conventionally been delivered in a hydrophilic vehicle, e.g. a hydrogel (aqueous gel). However, even though hydrogels have good patient compliance, a major problem with hydrogels when used in a bioadhesive formulation, is that said formulations have a tendency of being dissolved and/or eroded by the natural bodily fluids at the administration site, whereby the reliability and effectiveness of the formulation is compromised.

It is accordingly preferred that the vehicle used in the mucoadhesive gel composition according to the invention is an oleogel, i.e. a gel obtained by gelling at least one oil-composition with the gel-forming agent, and that the bioadhesive agent is dissolved, dispersed or suspended in said oleogel.

However, the bioadhesive may also be added to the oil-composition before gel formation, as this may provide a more homogenous vehicle.

Due the hydrophobic nature of an oleogel, an oleogel vehicle will not be dissolved/washed away by the bodily fluids as easily as an aqueous vehicle, and therefore offers the advantages of an increased residence time at the administration site, and thereby a more reliable drug delivery system.

The oil-composition(s) used for preparing the oleogel may be the same as disclosed in European patent publication nos. 1083880 and/or 2120865, and is preferably selected from mono-, di-, and triglycerides of synthetic, semi-synthetic and natural origin, and mixtures thereof, e.g. a mixture of capric/caprylic triglycerides. In a preferred embodiment, the vehicle is prepared by mixing liquid paraffin with petrolatum, and gelling said mixture with a suitable gel-forming agent e.g. carboxymethyl cellulose.

Since a water insoluble vehicle, as an oleogel vehicle, may retard release of certain API's from the bioadhesive gel composition, it may in some embodiment be preferred to provide a vehicle including small concentrations of a water soluble material, thereby quicken release of the specific API's.

In one embodiment, the vehicle may preferably comprise both a hydrogel (aqueous gel) and an oleogel, e.g. in the form of a bigel. A bigel is a uniform semisolid dispersion system that visually appear as a single gel, but in which an oleogel and an aqueous gel, are mixed together e.g. by applying a high shear rate. Bigels are not emulsions, and one of the major advantages of bigels is the improved stability compared to emulsions (water-in-oil and oil-in-water), emulgels, aqueous gels and oleogels, which makes bigels a potent vehicle for therapeutic agents. The enhanced physicochemical stability of the bigels can be attributed to the formation of extra fine colloidal dispersions, which is due to the immobilization of one gel (e.g. the aqueous gel) in a three-dimension gel network of the other gel (e.g. the oleogel). On storage at room temperature, the two components of the bigel do not get separated and the bigel therefore remains stable.

Further, no separation of the aqueous gel and oleogel is detected when a bigel is applied to the mucous. Thus, by converting oleogels and aqueous gels into bigels, a good patient compliance is provided without compromising the beneficial effects of the individual water and oil phases, as such bigels may comprise both hydrophilic and hydrophobic APIs. It has further been shown that the amalgamation of two gels may possess synergistic effect, resulting in improve drug permeation over the epithelium, due to the presences of both hydrophilic and lipophilic properties, i.e. the ingredient (s) in a bigel may penetrate though the mucosal tissue easier.

A bigel is normally obtained by preparing the aqueous gels and oleogels individually, after which the two gels are mixed together e.g. by applying a high shear rate. Examples of methods for formulating such bigels are e.g. disclosed in European patent publication nos. 1083880 and 2120865, and will not be discussed in further details in this application. The bioadhesive is preferably added to the oil-composition of the oleogel, before gel-formation.

Since it is preferred to include only relatively small amounts of water soluble materials in the gel composition according to the invention, the amount of aqueous gel in the vehicle is preferably below 20% by weight of the total weight of the vehicle, more preferably below 10% by weight of the total weight of the vehicle, and even more preferred below 5% by weight of the total weight of the vehicle.

It is however preferred to exclude water soluble materials from the mucoadhesive gel composition according to the invention, and if such materials are added, ensuring that said water soluble materials are only part of the gel composition at a relatively low concentration, e.g. below 5% by weight of the final mucoadhesive gel composition, preferably below 2.5% by weight of the final mucoadhesive gel composition, and even more preferred below 1% by weight of the final mucoadhesive gel composition. It is further preferred to provide a mucoadhesive gel composition substantially free and preferably completely free of volatile agents, as such volatile agents may compromise the gel composition ability to be retained at the site of administration by increasing the water-erodability of the compositions.

It is furthermore preferred that the gel composition does not comprise any surfactants and/or substances known to cause mucosal irritation.

Bioadhesive Agent.

The mucoadhesive pharmaceutical gel composition according to the invention also comprises one or more bioadhesives. The bioadhesive enables the pharmaceutical gel to adhere to the mucosal site of application, thereby extending residence time at the administration site, e.g. to buccal, nasal, vaginal and rectal mucosal tissue, to improve penetration of the therapeutic agent (API) through the mucosal membrane, control the erosion of the pharmaceutical gel composition to thereby control the release of the therapeutic agent, or control the dissolution kinetics of the therapeutic agent e.g. when wetted by saliva in the mouth. Moreover, by providing secure adhesion to the site of application, the bioadhesive agent enhances patient acceptability. The amount of bioadhesive in the gel composition constitutes 0.1-40% by weight; and in some cases, 25-35% by weight.

There is a variety of polymer materials that could be used as the bioadhesive agent. The bioadhesive agent may preferably comprise numerous hydrogen bond-forming groups (such as hydroxyl, thiol, carboxyl, or amine groups) that favor adhesion to the specific mucous layer where the gel composition should adhere. These interactions also depend on the pH and ionic composition in the mucous environment, and a person skilled in the art will understand that the bioadhesive may be selected depending on the administration site, i.e. one bioadhesive may be preferred for buccal administration, e.g. a bioadhesive which is not decomposed by e.g. α-amylase, and a different bioadhesive may be selected for vaginal administration. The bioadhesive could also serve as a pharmaceutical binder to provide necessary bonding of the ingredients within the gel formulation.

The bioadhesive may comprise any of a variety of different types of natural, synthetic, or biological polymers; lipids; phospholipids; or the like. Polymer materials that could be used as the bioadhesive agents in the pharmaceutical gel composition include the following: Cellulose derivatives such as methyl cellulose, ethyl cellulose, methylethyl cellulose, hydroxymethyl cellulose, hydroxyethyl cellulose, hydroxypropyl cellulose (HPC), hydroxyethylmethyl cellulose, hydroxypropylmethyl cellulose (HPMC), ethylhydroxyethyl cellulose, hydroxypropylmethyl cellulose phthalate, or carboxylated cellulose derivatives such as carboxymethyl cellulose (CMC). Natural gum materials such as karaya gum, acacia gum, tragacanth gum, guar gum, or xanthan gum. Proteins such as gelatin, collagen, or lectins. Polysaccharides such as chitosans, pectin, sodium alginate, hyaluronic acid, agarose, dextran, or starch. Synthetic polymers such as vinyl ether polymers and copolymers, poly(ethylene oxide), poly(vinyl pyrrolidine), poly (ethylene glycol), poly(vinyl alcohol), methacrylates polymers, such as poly(hydroxyethyl methacrylate), and poloxamers, which are nonionic block copolymers based on ethylene oxide and propylene oxide (such as the Pluronic® product line).

Among the various polymer materials that could be used as the bioadhesive, poly(acrylic acid)-containing polymers of acrylic acid may be particularly suitable in the pharmaceutical gel composition according to the invention. Poly (acrylic acid)-containing polymers have excellent bioadhesive characteristics because the carboxylic acid groups form strong hydrogen bonds with the oligosaccharide chains on mucosal and tissue surfaces. Poly(acrylic acid)-containing polymers are available in a wide range of molecular weights, are non-toxic, and are generally considered safe.

There are a variety of different types of poly(acrylic acid)-containing polymers that could be used as the bioadhesive. For example, the poly(acrylic acid)-containing polymer could be homopolymers of acrylic acid, or crosslinked with a crosslinking agent, such as an allyl ether of pentaerythritol, allyl ether of sucrose, allyl ether of propylene, polyalkenyl ethers, or divinylglycol; sometimes referred to as carbomers (such as the Carbopol® product line) or polycarbophil (such as the Noveon® product line).

Another polymer material that may be particularly suitable for use as the bioadhesive is poly(methyl vinyl ether-co-maleic anhydride) (PVM/MA), such as the Gantrez™ product line of monoalkyl esters of PVM/MA. Other examples of bioadhesives that could be used include the adhesive materials used in denture fixatives or adhesives, such as those described in U.S. Pat. No. 5,302,628 (Richard Lim et al), U.S. Pat. No. 5,696,181 (Tiang-Shing Chang et al), U.S. Pat. No. 6,350,794 (Michael Borja), and U.S. Pat. No. 7,517,920 (Akihiro Sudo). The material used as the bioadhesive in this invention may be cross-linked and the density of cross-linking may vary depending on the particular situation. The pharmaceutical gel according to the invention may contain one or more different bioadhesives in any combination.

Gel-Forming Agent.

The vehicle of the pharmaceutical mucoadhesive gel composition further comprises one or more gel-forming agents. As used herein, the term "gel-forming agent" means a material that is capable of forming a gel when exposed to aqueous media. A gel is a swollen or swellable polymer matrix, which may be crosslinked. The amount of gel-forming agent in the gel composition constitutes 0.5-30% by weight; and in some cases, 15-25% by weight. The gel is accordingly formed before application to the administration site, i.e. said gel is not formed in situ. The gel matrix may serve to physically entrap the API, i.e. the therapeutic agent molecules for subsequent slow release by diffusion or erosion. This may make it possible for the pharmaceutical gel composition to release the therapeutic agent at a rate with near zero-order kinetics. As such, in some embodiments, the gel composition is arranged for releasing the therapeutic agent with zero-order or near zero-order kinetics over at least 6 hours duration; and in some cases, at least 10 hours duration. In some embodiments, the gel composition releases the therapeutic agent with zero-order or near zero-order kinetics over the release of at least 30% of the mass of the therapeutic agent contained in the gel composition; and in some cases, at least 50% of the mass. As used herein, the term "zero-order kinetics" means that a constant amount of the therapeutic agent (e.g. X milligrams per unit time, as opposed to a constant percentage of the amount remaining) is released from the gel composition over a period of time when tested in pH 7.4 aqueous media at about 23° C.

How well the release rate conforms to zero-order kinetics can be assessed by performing a least squares best-fit of the line $QT=Q0+KT$ through the plot of amount released over time, where QT is the cumulative amount of therapeutic agent released at time T, Q0 is the initial amount of therapeutic agent released at time T=0, and K is the release kinetic constant. The term "near zero-order kinetics" means that the value of the correlation coefficient in the least squares best-fit line is at least 0.7. Calculation of a correlation coefficient is a conventional statistical technique for assessing the quality of a least squares fitting to the data.

The gel-forming agent may be any of those materials identified above for the bioadhesiveness. Other materials that could be used for the gel-forming agent are inorganic materials such as colloidal magnesium-aluminum silicates or silica gel. The pharmaceutical gel composition according to the invention may contain one or more different gel-forming agents in any combination.

In a preferred embodiment, especially if the vehicle is a bigel, is a gel-forming agent comprising a combination of ethylcellulose, propylene glycol isostearate and propylene glycol laurate in relative proportions of 8:2:90% by weight (wt %), respectively. An example of such a formulation is Emulfree®, obtainable from Gattefosse.

In some embodiments, the gel-forming agent is a C1-C4 alkyl cellulose derivative (such as ethyl cellulose, methyl cellulose, or hydroxypropyl cellulose, including salts thereof). In some embodiments, the gel-forming agent is a C1-C4 carboxyalkyl cellulose derivative (such as carboxymethyl cellulose). In some embodiments, the C1-C4 carboxyalkyl cellulose derivative is non-salt-containing carboxyalkyl cellulose, i.e. carboxyalkyl cellulose in free acid form in which the salt is removed. C1-C4 carboxyalkyl cellulose (e.g. carboxymethyl cellulose) in free acid form has the advantage of being less water-soluble, thereby forming a higher viscosity gel that forms a stronger three-dimensional network structure. This increase in viscosity can support a more sustained and controlled release of the therapeutic agent.

It is preferred that the gel composition according to the invention has a viscosity in the range of about 139.5 Pa·s (pascal seconds) to about 418.5 Pa·s, e.g. about 280 Pa·s (as measured by a Rheomat RM 100, measure system MS-R4, at a shear rate of $0.37\ s^{-1}$, and performed at 21° C.), as this ensures that the composition easily can be applied/distributed/spread on the relevant mucosal tissue, but also that the composition is stiff enough to prevent the composition from leaking/dripping and/or be displaced after application.

Other Properties & Ingredients.

There is some overlap between the materials that could be selected for the bioadhesive and the gel-forming agent. That is, some materials could be selected as either a bioadhesive or a gel-forming. However, in preferred embodiments, the bioadhesive is different from the gel-forming agent. In some embodiments, the bioadhesive agent has greater adhesive strength than the gelling agent. A variety of mechanical tests have been used to compare the adhesive strength of bioadhesive materials. See Peppas et al, "Hydrogels as bioadhesive and bioadhesive materials: a review" (1996) Biomaterials 17:1553-1561. Any of such tests could be used to compare a selected bioadhesive against a selected gel-forming agent for adhesive strength.

A high gel strength ensures that the gel composition according to the invention is retained at the administration site for the required/necessary treatment period, i.e. until the desired amount of API, e.g. at least 50% by weight of the API contained in the administered dosage has entered the systemic circulation.

The vehicle and/or pharmaceutical gel composition may also contain other ingredients that are suitable for use in buccal drug formulations. For example, if the pharmaceutical gel composition according to the invention is intended for buccal administration, said gel may e.g. comprise flavoring agents such as peppermint oil, wintergreen oil, spearmint oil, cinnamaldehyde, cetyl pyridinium chloride, menthol saccharin sodium, glycyrrhizin, malt syrup, citric acid, tartaric acid, lemon oil, citrus flavor, and the like.

Therapeutic Agent.

Any therapeutic agent capable of crossing a mucosal membrane, e.g. the buccal, nasal, vaginal and rectal mucosal membrane, and are known to be metabolized by the liver may be suitable for use in the pharmaceutical mucoadhesive gel composition according to the invention. The term "therapeutic agent" refers to one or more active pharmaceutical ingredient(s) and are in the present application used interchangeable with the term active pharmaceutical ingredient, and encompasses any pharmaceutically acceptable salt thereof. In some embodiments, the therapeutic agent constitutes 1-30% by weight of the gel composition; in some cases, 1-15% by weight. The therapeutic agent may be provided in particulate form. For example, the therapeutic agent may be micronized or nanonized (made into nano-sized particles), preferably having an average size in the range from about 0.001 nm to about 500 μm, more preferred an average size from about 0.01 nm to about 100 μm, and even more preferred an average size from about 0.05 nm to about 40 μm.

Therapeutic agents that are more lipophilic may more easily cross the buccal mucosal membrane. As such, in some embodiments, the therapeutic agent has a water solubility of less than 50 mg/L at 25° C.; in some cases, less than 30 mg/L at 25° C.; and in some cases, less than 20 mg/L at 25° C.

Therapeutic agents having relatively high potency (therapeutic efficacy at low dose amounts) may be particularly suitable for use in this invention. As such, in some embodiments, the therapeutic agent is one that is therapeutically effective at 1,000 μg or less in a single dose; in some cases, 500 μg or less in a single dose; and in some cases, 100 μg or less in a single dose.

An example of a high potency therapeutic agent that could be used in the invention is desmopressin acetate (e.g. for the treatment of nighttime bedwetting in children). The weight of a unit dosage of such a gel composition is preferably about 0.1 g, and preferably comprises between 0.1 mg and 1.5 mg of desmopressin acetate, and is preferably arranged for buccal administration.

Steroidal hormones are both relatively lipophilic and have relatively high potency when used as medications. As such, in some embodiments, the therapeutic agent is a steroidal hormone. Examples of steroidal hormones that could be used include testosterone, dihydrotestosterone (DHT), estradiol, ethinylestradiol, estrone, estrone sulfate, progesterone, levonorgestrel, desogestrel (a synthetic progesterone), danazol, combinations of sex steroidal hormones, sepranolol and selective progesterone modifiers, and the like. As used herein, the term "steroidal" means a compound having the well-known steroid core structure of seventeen carbon atoms, bonded in four "fused" rings (six-member rings A, B, and C, and a five member ring D). In some embodiments, the therapeutic agent is progesterone and constitutes 1-20% by weight of the gel composition; in some cases, 1-15% by weight. In some embodiments, the therapeutic agent is estradiol and constitutes 0.01-5% by weight of the gel composition. In some embodiments, the therapeutic agent is testosterone and constitutes 0.1-12% by weight of the gel composition.

Orally administered medications are subject to gastrointestinal degradation by acid or enzymes. As such, the administered pharmaceutical gel composition of the invention may be particularly suitable for therapeutic agents that are vulnerable to gastrointestinal degradation, such as proteins or peptide therapeutic agents. As such, in some embodiments, the therapeutic agent is a protein or peptide.

Examples of therapeutic agents that could be used in the gel composition is shown in Table A below:

TABLE A

Proteins and peptides, such as GnRH (agonist and antagonist), oxytocin and analogs, somatostatin and analogs, tissue plaminogen activator (TPA), growth hormone releasing hormone (GHRH), corticotropin-releasing hormone (CRH) and analogs, insulin, glucagon like peptide, ghrelin and analogs, follicle-stimulating hormone (FSH), luteinizing hormone (LH), human chorionic gonadotropin (HCG), thyroid-stimulating hormone (TSH), and the like.
Steroidal hormones, such as testosterone, dihydrotestosterone (DHT), ethinylestradiol, estrone, estrone sulfate, estradiol, or progestins, such as progesterone, levonorgestrel, desogestrel, Danazol, combinations of sex steroidal hormones, sepranolol and selective progesterone modifiers; and the like
Anti-hormones, such as tamoxifen, endoxifen, mifepristone, and the like.
Nitrates, such as nitroglycerin, isosorbide, erythrityl tetranitrate, pentaerythritol tetranitrate, and the like.
β-adrenergic receptor agonists, such as terbutaline, albuterol, pirbuterol, bitolterol, ritodrine, and the like.
β-adrenergic receptor antagonists, such as propranolol, metoprolol, nadolol, atenolol, timolol, esmolol, pindolol, acebutolol, labetalol, and the like.
Opioids, such as morphine, hydromorphone, oxymorphone, codeine, hydrocodone, oxycodone, levorphanol, levallorphan, butophanol, buprenorphine, fentanyl, nalbuphine, butorphanol, pentazocine, methadone, etorphine, sufentanil, [D-Ala2, N-MePhe4, Gly-ol]-enkephalin (DAMGO), naloxone, naltrexone, D-Phe-Cys-Tyr-D-Trp-Orn-Thr-Pen-Thr-NH2 (CTOP), diprenorphine, β-funaltrexamine, naloxonazine, nalorphine, and the like.
Opioid-antagonists, such as naloxone, nalmefene, and the like.
Antidepressants, such as amitriptyline, amoxapine, desipramine, doxepin, imipramine, maprotilen, nortriptyline, protripyline, trimipramine, fluoxetine, trazodone, and the like.
HMG CoA reductase inhibitors, such as lovastatin, mevastatin, simvastatin, pravastatin, atorvastatin, and the like.
Antihistamines, such as loratadine, chlorpheniramine maleate, brompheniramine maleate, diphenhydramine, dimenhydrinate, carbinoxamine, promethazine, tripelannamine, and the like.
ACE inhibitors, such as captopril, enalapril, lisinopril, and the like.
Prostaglandins, such as misoprostol and the like.
Cannabinoids.
Minerals and vitamins, especially iron.
Nicotine receptor antagonist, e.g. varenicline, bupropion, and cytisine
5-α-reductase inhibitors Dosage Form.

The pharmaceutical mucoadhesive gel composition according to the invention may be provided in any suitable unit dose or multi-dose form. In some embodiments, the invention is a pharmaceutical product comprising a single-use disposable applicator arranged for easy administration of the gel composition to relevant mucosal tissue, e.g. nasal, vaginal, buccal, and rectal tissue.

Contained in the disposable applicator is the pharmaceutical gel composition of the invention. Each single-use applicator contains at least the amount needed for a single dose of the pharmaceutical gel composition; but it is preferred that the applicator contains a unit dosage of the gel composition.

Within the context of the present invention the term "unit dosage" means the dosage delivered to the administration site, and since it must be expected that a part of the gel composition according to the invention is cleared/removed by the natural body fluids, said unit dosage may preferably comprise a larger amount of therapeutic agent than necessary if all therapeutic agent were delivered to systemic circulation, i.e. a unit dosage is the amount of a single dosage, plus a reserve amount of 5-50% of the single dosage amount to ensure that an adequate plasma concentration of the therapeutic agent is provided. For example, the single-use applicator may contain a unit dosage comprising between about 0.4 and 1.5 grams of the pharmaceutical gel composition, containing between about 40-225 mg of the therapeutic agent, where the required plasma dosage is in the range of 30-150 mg, i.e. the amount required for obtaining the desired plasma concentrations of the API if the therapeutic agent were administered intravenous. In some embodiments, the single-use applicator contains greater than the amount of therapeutic agent needed for plasma dosage, but less than the amount needed for two dosage.

In some embodiments, the dosage form is a metered-dose dispenser containing multiple doses of the gel composition. The metered-dose dispenser contains the amount needed for multiple doses of the gel composition. Each activation of the metered-dose dispenser dispenses a unit dose of the gel composition for application by the user, e.g. about 0.4 to 1.5 g.

Medical Conditions.

The pharmaceutical formulation of this invention may be used for the treatment of any medical condition that is conventionally treated by the selected therapeutic agent. In the case of progesterone, the pharmaceutical formulation of this invention may be used for the treatment of any medical condition conventionally treated with progesterone. As used herein, the term "treatment for female infertility disorders" includes treatments for female infertility, corpus luteum insufficiency, fetal maturation, support in maintaining a pregnancy, and as part of assisted reproduction or infertility procedures.

In some embodiments, the pharmaceutical mucoadhesive gel composition of the invention is used to induce a secretory endometrium in the patient. Inducing a secretory endometrium is effective in treating female infertility disorders or treating cancers such as cervical cancer or breast cancer, or preventing endometrial cancer in patients undergoing postmenopausal hormone replacement therapy. In some embodiments, the medical condition is breast cancer; in some cases, the breast cancer is estrogen receptor positive breast cancer; in some cases, the breast cancer is estrogen receptor positive and progesterone receptor positive breast cancer.

In some embodiments, the medical condition is a hormone-related gynecological condition. Examples of such include menopausal symptoms (such as in postmenopausal hormone replacement therapy), premenstrual syndrome (PMS), endometriosis, low sex hormones, low testosterone, or polycystic ovarian syndrome (PCOS). Prior buccal formulations of drugs have been used for local pathology in the mouth, such as ulcers or infections. It is however preferred, that the pharmaceutical gel composition of the present invention is not used for locally treating a medical condition in the oral cavity.

Method of Use.

The pharmaceutical mucoadhesive gel composition may be applied to any suitable mucosal surface e.g. a buccal surface in the mouth, such as the gingival pouch (anatomically referred to as the vestibule). In some embodiments, the pharmaceutical gel is applied to the gingival pouch (upper or lower). The pharmaceutical gel may be dosed in any suitable manner to achieve a therapeutic effect. The patient may receive intermittent dosing. In some embodiments, the dosing frequency is twice a day, e.g. every about 12 hours.

In a preferred embodiment, the gel composition according to the invention is administered via a patch or film, preferably made of a material that will degrade and/or dissolved when contacted by bodily fluids at the administration site. This has the advantage that the user always will apply the correct amount of gel composition to the administration site, e.g. 0.5 grams.

The dosing regimen should result in sufficiently high levels of the therapeutic agent in the systemic circulation. If the therapeutic agent is progesterone, the pharmaceutical gel is dosed to achieve an amount of therapeutic agent in the plasma or serum of at least 5 ng/mL; in some cases, at least 8 ng/mL; in some cases, at least 11 ng/mL; and in some cases, at least 15 ng/mL. This high level of progesterone may be sustained for a sufficient duration of time for therapeutic effectiveness. In some cases, this high level of progesterone is sustained for at least 6 hours duration after dosing; and in some cases, at least 12 hours duration after dosing.

Because the pharmaceutical gel is adherent to the mucosal surface, and only contains small amounts of volatile solvents and/or water soluble materials (if any), it will have extended residence time at the site of application e.g. in the oral cavity. In some embodiments, the pharmaceutical gel is maintained at the site of application for at least 4 hours duration; and in some cases, at least 6 hours duration.

Because the pharmaceutical gel is adherent to the mucosal surface, it may be useful for overnight dosing. In some embodiments, the pharmaceutical gel is maintained e.g. in the oral cavity while the patient is asleep. In some embodiments, the pharmaceutical gel is applied at the patient's bedtime or at a time that is within 60 minutes before (e.g. instructed to apply 30 minutes before bedtime).

Preferred Embodiment of a Mucoadhesive Gel Composition for Buccal Administration.

In a preferred embodiment, the vehicle is an oleogel comprising petrolatum, in an amount that constitutes 15-25% by weight of the final gel composition, and liquid paraffin in an amount that constitutes 15-25% by weight of the final gel composition.

As a bioadhesive said gel composition comprises Gantrez™ MS 955 polymer product (mixed sodium and calcium salt of PVM/MA copolymer) in an amount that constitutes 25-35% by weight of the final gel composition; carboxymethyl cellulose (CMC) as the gel-forming agent in an amount that constitutes 15-25% by weight of the final gel composition, and optionally silica (as a gel-forming agent) in an amount that constitutes 0.1-1% by weight of the final gel composition.

The gel composition may e.g. comprise micronized progesterone in an amount between 8 and 20% by weight of the final gel composition.

The invention is described below with the assumption that the applicator according to the present invention is intended for buccal administration. However, modifications of said applications, e.g. different shapes of the tip, in order to facilitate administration to e.g. the vaginal, rectal or nasal cavity is also contemplated within the scope of the invention. It is preferred that the device has a size, which facilitates administration by a single hand.

FIG. 1 shows an example of a single-use disposable applicator 10. The applicator 10 is filled with the gel composition. There is a cap 12 at the tip of the applicator 10. A plunger 14 is 20 pressed to dispense the gel composition from the tip of the applicator 10. The user removes the cap 12 and positions the tip of the applicator 10 onto the target site in the oral cavity. The user pushes on plunger 14 to dispense a unit dose of the pharmaceutical gel to the target site.

Figure 2:
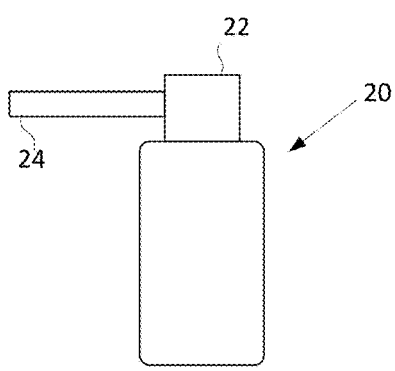
FIG. 2 shows an example of a metered-dose dispenser filled with a gel composition of the invention.

FIG. 2 shows an example of a metered-dose dispenser 20 filled with multiple dose amounts of the pharmaceutical gel composition. The dispenser 20 has a pump head 22 and a long dispensing spout 24. The user positions the tip of spout 24 onto the target site in the oral cavity. The user pushes down on the pump head 22, which dispenses a preset amount of the pharmaceutical gel out of the spout.

Experimental Examples.

The general procedure for making the batches of micronized progesterone gel was as follows. Make the vehicle by mixing liquid paraffin, obtained at 40° C. with petrolatum obtained at 40° C. (and optionally, mint oil obtained at 40° C.) under magnetic stirring. Add the bioadhesive Gantrez™ MS-955 product obtained at 35° C. (mixed sodium and calcium salt of PVM/MA copolymer) and disperse into the mixture using a motorized mixer for 15 min between 300 and 1100 rpm. Optionally, add silica to the preparation with the motorized mixer obtained at 35-40° C. for 5 min at 1000 rpm. Add the gel-forming agent carboxymethyl cellulose (CMC, Blanose™ product, obtained at 35-40° C.) to the preparation with further mixing for 10 min in order to prepare a vehicle for carrying the therapeutic agent, progesterone. Introduce micronized progesterone, obtained at obtained at room temperature and mix to disperse thoroughly into the mixture.

Ten batches of the mucoadhesive progesterone gel composition were made. Table 1 shows the composition of the batches. Table 2 shows the composition, in percentage terms, of selected batches that were tested in-vivo.

TABLE 1

| | Batch (amounts in grams) | | | | | | | | |
|---|---|---|---|---|---|---|---|---|---|
| | #1, 2 | #3 | #4 | #5 | #6 | #7 | #8 | #9 | #10 |
| Bioadhesive: PVM/MA copolymer | 63.0 | 32.7 | 32.7 | 32.7 | 32.7 | 32.8 | 32.6 | 32.6 | 28.3 |
| Oil-compound: petrolatum | 20.5 | 21.8 | 21.8 | 21.8 | 21.8 | 21.9 | 21.8 | 21.8 | 24.0 |
| Oil-compound: liquid paraffinum | 21.5 | 23.4 | 23.4 | 23.4 | 23.4 | 23.5 | 23.4 | 23.4 | 27.0 |
| Gel-forming agent: CMC | 20.0 | 21.8 | 21.8 | 21.8 | 21.8 | 21.9 | 21.8 | 21.8 | 20.5 |
| mint oil | | | | | | | 0.5 | 0.5 | |
| Gel-forming agent: silica | 0.26 | 0.27 | 0.27 | 0.27 | 0.27 | | | | 0.20 |
| API: progesterone, micronized* (w/w) | 8% | 8% | 12% | 15% | 20% | 20% | 20% | 20% | 8% |

*For batches #1-3, 1.2 g of micronized progesterone was mixed into 13.8 g of vehicle to result in an 8% mixture. For batch #4, 1.8 g of micronized progesterone was mixed into 13.2 g of vehicle to result in a 12% mixture. For batch #5, 2.3 g of micronized progesterone was mixed 5 into 12.8 g of vehicle to result in a 15% mixture. For batches #6-9, 3.0 g of micronized progesterone was mixed into 12.0 g of vehicle to result in an 20% mixture. For batch #10, 1.2 g of micronized progesterone was mixed into 13.8 g of vehicle to result in an 8% mixture.

TABLE 2

| | #2 | #9 | #10 |
|---|---|---|---|
| PVM/MA copolymer | 30.1% | 26.1% | 26.0% |
| Petrolatum | 20.1% | 17.4% | 22.1% |
| liquid paraffin | 21.6% | 18.7% | 24.8% |
| CMC | 20.1% | 17.4% | 18.9% |
| mint oil | | 0.40% | |
| silica | 0.25% | | 0.18% |
| progesterone, micronized | 8% | 20% | 8% |

Figure 3:
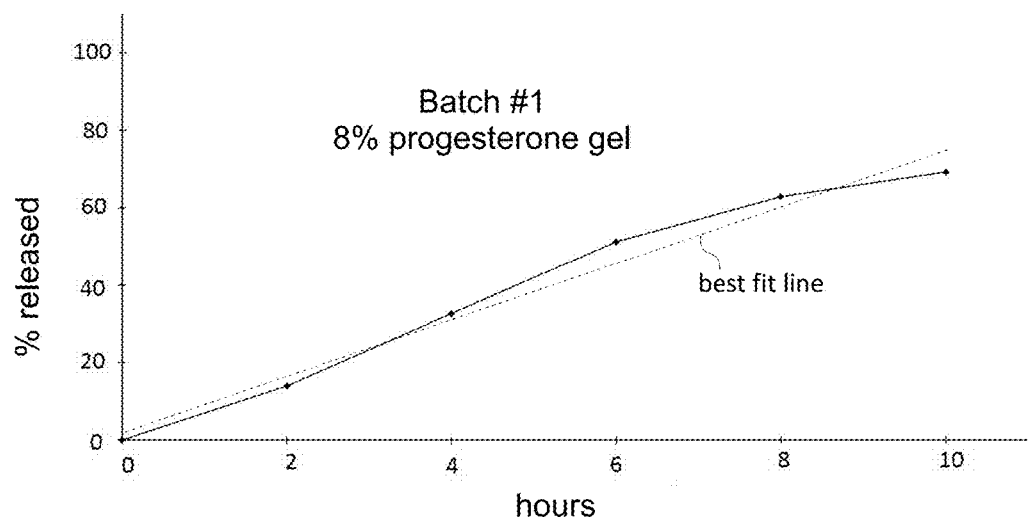
FIG. 3 shows the in-vitro drug release profile of 8% progesterone gel batch #1.

The drug release rates from the batches #1, #3, #4, #5, #6, #7, #8, and #10 were tested in-vitro. Gel samples were made by pouring 0.40 grams of the selected batch in a 125 mL glass bottle. 100 mL of a 0.5% SDS (sodium dodecyl sulfate) pre-heated solution were added to the bottles and then kept at 37° C. Test samples (5 mL) were taken at two hours intervals. The solutions were then assayed for progesterone concentration using UV spectrophotometry at 251 nm. The result for batch #1 is shown in FIG. 3. Also shown in FIG. 3 is a dotted line as a hypothetical example of a least squares best-fit line through the plot, which exhibits near zero-order kinetics with the correlation coefficient of the best-fit line being at least 0.7.

Figure 5:
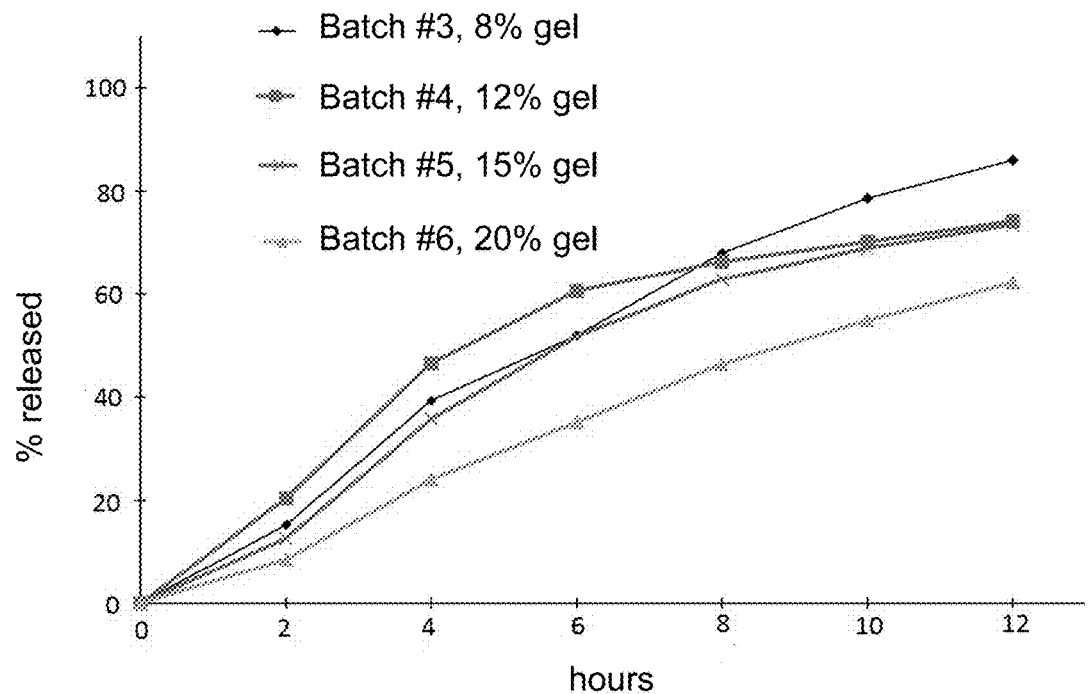
FIG. 5 shows the in-vitro drug release profile of progesterone gel batches #3, #4, #5, and #6.
Figure 6:
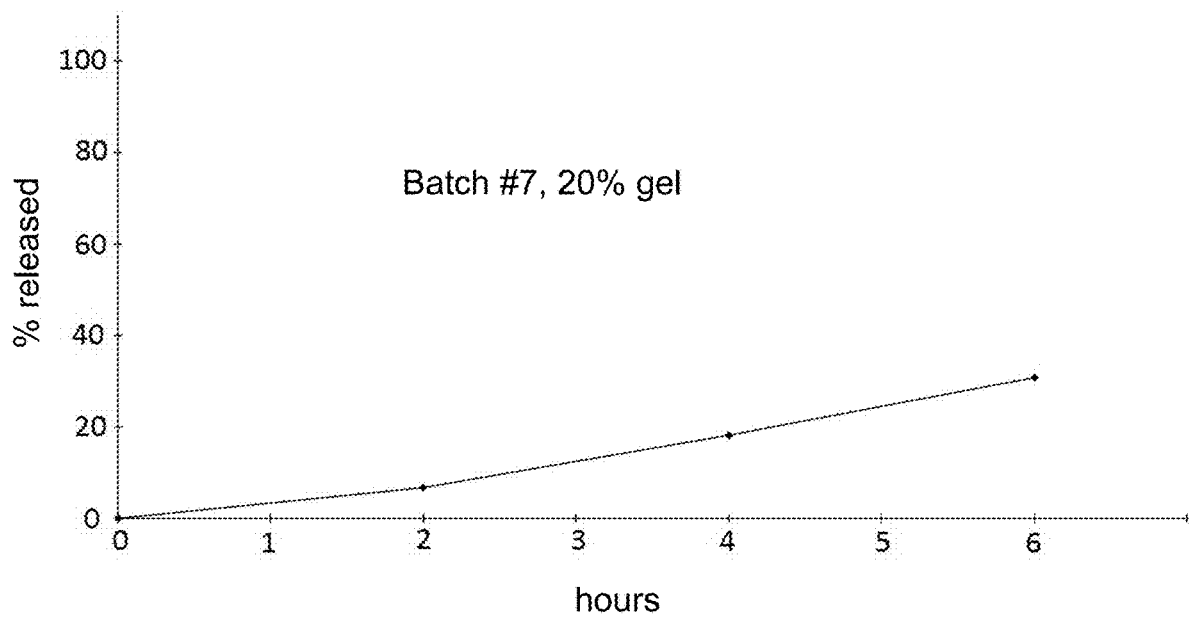
FIG. 6 shows the in-vitro drug release profile of 20% progesterone gel batch #7.
Figure 7:
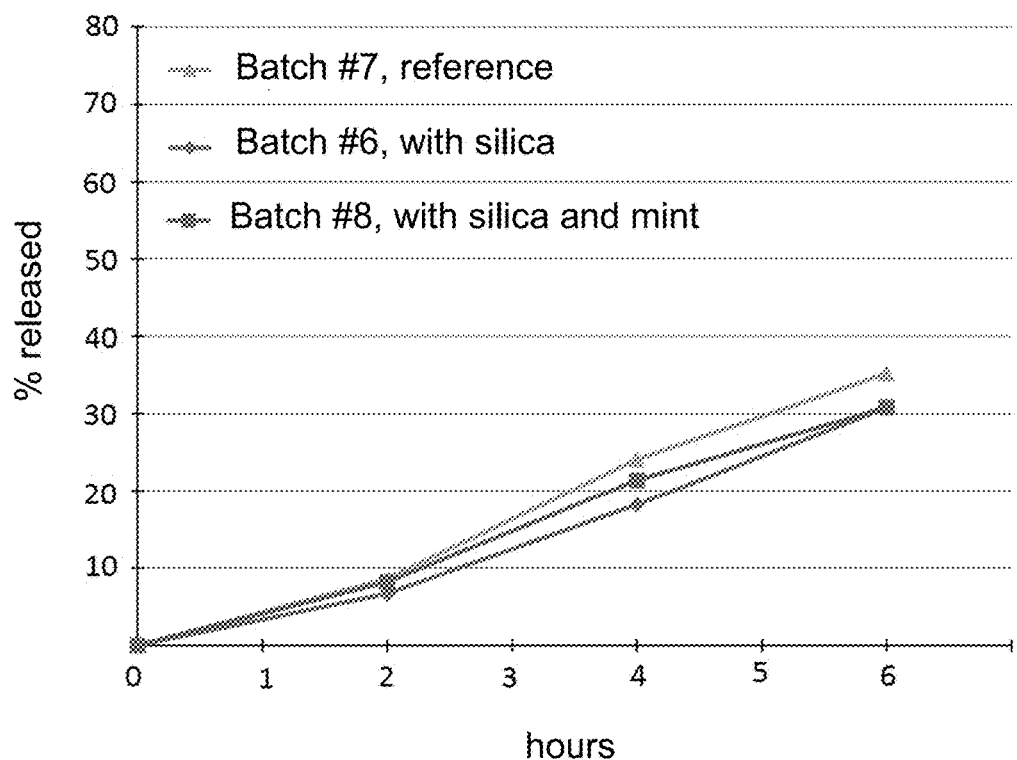
FIG. 7 shows the in-vitro drug release profile of 20% progesterone gel batch #8.
Figure 9:
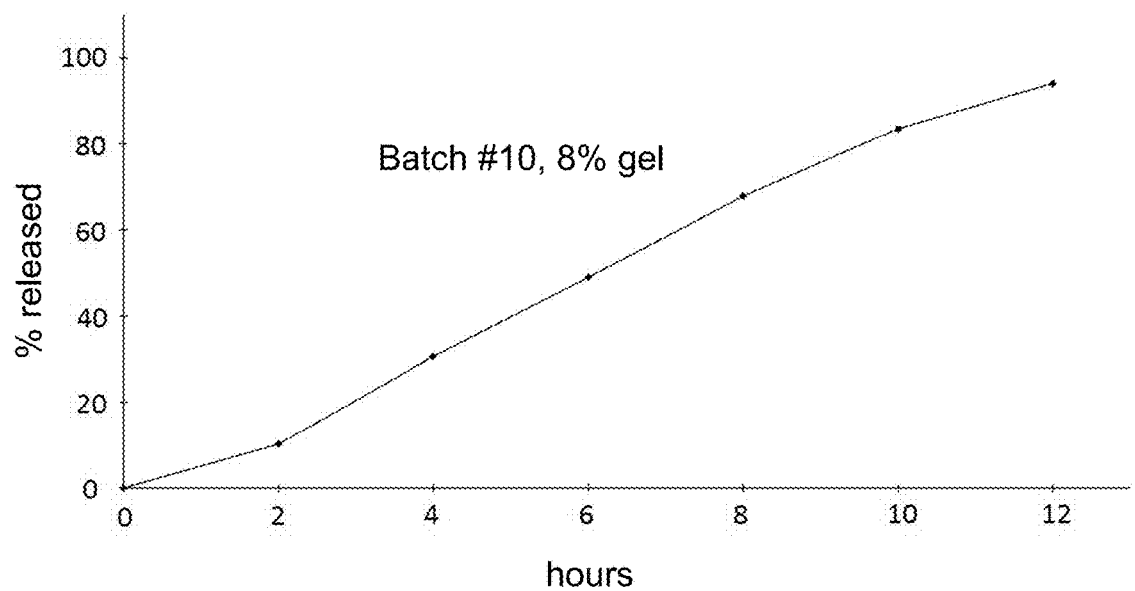
FIG. 9 shows the in-vitro drug release profile of 8% progesterone gel batch #10.

The results for batches #3, #4, #5, and #6 are shown in FIG. 5. The result for batch #7 is shown in FIG. 6. The result for batch #8 is shown in FIG. 7. The result for batch #10 is shown in FIG. 9.

Figure 4:
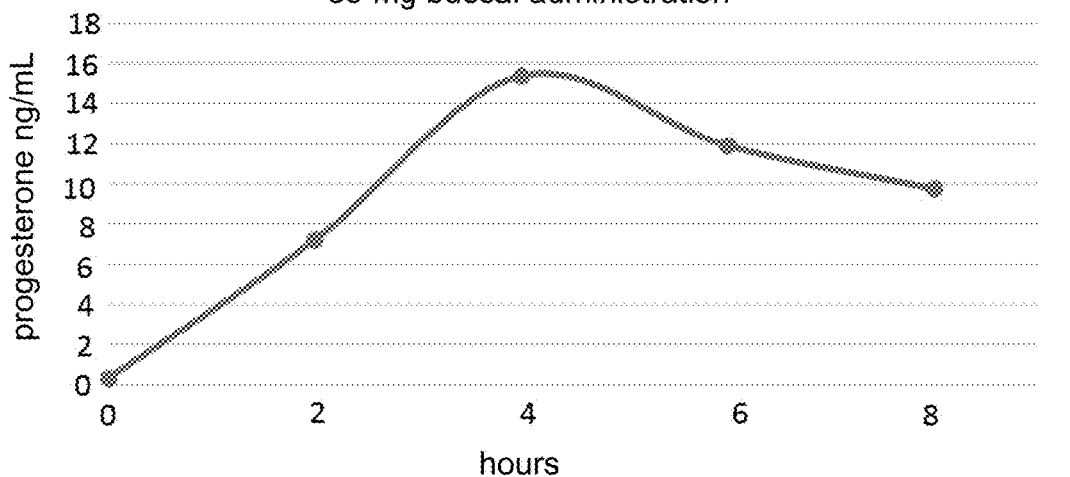
FIG. 4 shows the in-vivo serum levels of progesterone in a subject who was administered 59 mg progesterone by applying 741 mg of 8% progesterone gel batch #2 to the inferior gingival cavity.

Batch #2 was tested in-vivo. 741 mg of the gel (containing 59 mg progesterone) was applied in the inferior gingival cavity of a test subject. Blood samples were taken every 2 hours and serum progesterone concentration was measured using electro-chemiluminescence immunoassay. The result is shown in FIG. 4.

Figure 8:
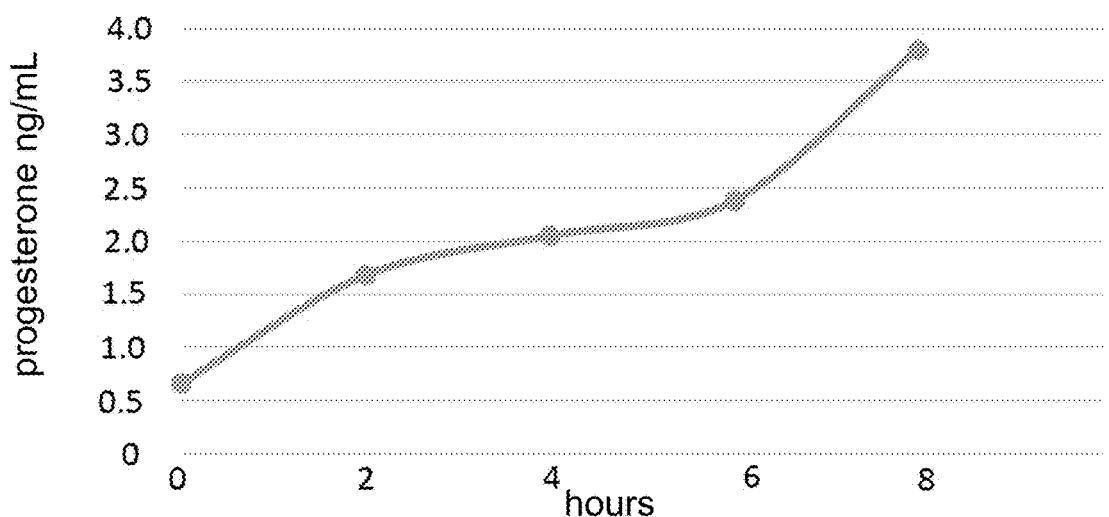
FIG. 8 shows the in-vivo serum levels of progesterone in a subject who was administered 60 mg progesterone by applying 300 mg of 20% progesterone gel batch #9 to the superior gingival cavity.

Batch #9 was tested in-vivo. 300 mg of the gel (containing 60 mg progesterone) was applied in the superior gingival cavity of a test subject. Blood samples were taken every 2 hours and serum progesterone concentration was measured using electro-chemiluminescence immunoassay. The result is shown in FIG. 8.

Figure 10:
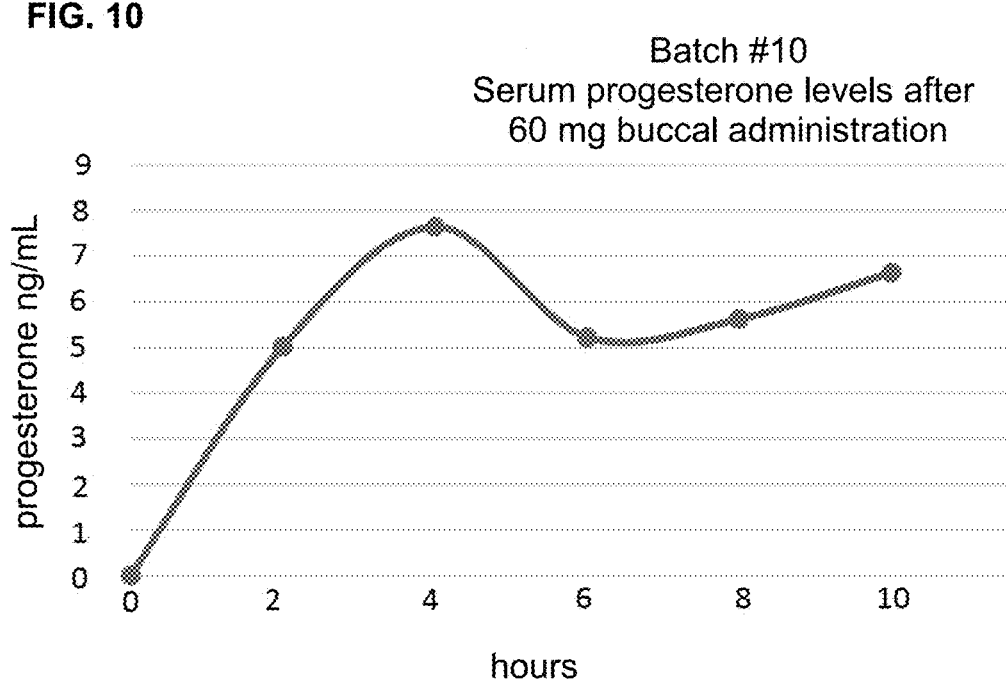
FIG. 10 shows the in-vivo serum levels of progesterone in a subject who was administered 60 mg progesterone by applying 2×375 mg of 8% progesterone gel batch #10 to the superior gingival cavity.

Batch #10 was tested in-vivo. 2×375 mg of the gel (containing 30 mg progesterone each) was applied in the superior gingival cavity of a test volunteer. Blood samples were taken every 2 hours for 10 hours and progesterone concentration was measured using electro-chemiluminescence immunoassay. The result is shown in FIG. 10. Also, the maximum of residual gel was collected and assayed for the amount of progesterone. 25% of the gel-composition was recovered, indicating that not more than 45.6 mg of progesterone was absorbed.

Furthermore, since 25% of the gel composition were still present in the oral cavity after 10 hours, it is clear that the resident time in the oral cavity is significant, likely due to the lack of water soluble materials and volatile agents in the gel composition according of he invention, thereby providing an improved gel composition compared to the known gel compositions.

Conclusion:

The foregoing description and examples have been set forth merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are contemplated within the scope of the invention.

The invention claimed is:

1. A stable pharmaceutical mucoadhesive gel composition, comprising:
    a) a vehicle comprising:
        (i) a gel-forming agent, wherein the gel-forming agent constitutes 0.5% up to 30% by weight of the stable pharmaceutical mucoadhesive gel composition;
        (ii) a bioadhesive agent, wherein the bioadhesive agent constitutes 0.5% up to 40% by weight of the stable pharmaceutical mucoadhesive gel composition; and
        (iii) an oil composition, wherein the oil composition comprises a mixture of liquid paraffin and petrolatum; and
    b) micronized progesterone, wherein the micronized progesterone is present in an amount of 1% up to 20% by weight of the stable pharmaceutical mucoadhesive gel composition,
    wherein the stable pharmaceutical mucoadhesive gel composition has a viscosity in the range of about 139.5 Pascal seconds (Pa·s) up to about 418.5 Pa·s at about 21 degrees Celsius.

2. The stable pharmaceutical mucoadhesive gel composition according to claim 1, wherein the oil-composition comprises the mixture of liquid paraffin, constituting between 20 and 30% by weight of the vehicle, and petrolatum constituting between 20 and 25% by weight of the vehicle.

3. The stable pharmaceutical mucoadhesive gel composition according to claim 1, wherein the vehicle further comprises an aqueous gel.

4. The stable pharmaceutical mucoadhesive gel composition according to claim 1, wherein the amount of aqueous gel in the vehicle is below 20% by weight of the total weight of the vehicle.

5. The stable pharmaceutical mucoadhesive gel composition according to claim 1, wherein the bioadhesive has a greater adhesive strength than the gel-forming agent as determined by a mechanical test.

6. The stable pharmaceutical mucoadhesive gel composition according to claim 1, wherein the bioadhesive agent comprises a mixed sodium and calcium salt of a poly(methyl vinyl ether-co-maleic anhydride) copolymer, or a poly(acrylic acid)-containing polymer.

7. The stable pharmaceutical mucoadhesive gel composition according to claim 1, wherein the gel-forming agent comprises a C1-C4 alkyl cellulose derivative, a ethyl cellulose, a methyl cellulose, a hydroxypropyl cellulose, a carboxymethyl cellulose, or a carboxyalkyl cellulose derivative.

8. The stable pharmaceutical mucoadhesive gel composition according to claim 7, comprising the carboxymethyl cellulose.

9. The pharmaceutical mucoadhesive gel composition according to claim 1, wherein the viscosity is measured by a Rheomat RM 100, measure system MS-R4, at a shear rate of 0.37 s$^{-1}$, and performed at 21° C.

10. The stable pharmaceutical mucoadhesive gel composition according to claim 1, that is formulated for buccal administration.

11. An applicator comprising a stable pharmaceutical mucoadhesive gel composition according to claim 1.

12. The applicator according to claim 11, wherein the applicator is configured for a single use.

13. The applicator according to claim 11, wherein the applicator contains a unit dosage of the micronized progesterone.

14. The applicator according to claim 11, wherein the applicator is a metered-dose dispenser configured for dispensing a unit dose of the stable pharmaceutical mucoadhesive gel composition for each activation.

15. The applicator according to claim 11, wherein the applicator is configured for buccal, nasal, vaginal, or rectal administration.

16. A method of administering a progesterone to a female patient by buccal delivery, comprising:
    providing a stable pharmaceutical mucoadhesive gel composition according to claim 1;
    contacting the stable pharmaceutical mucoadhesive gel composition onto a mucosal site in the patient's oral cavity;
    wherein the stable pharmaceutical mucoadhesive gel composition is formulated for achieving a plasma or serum progesterone level of at least 5 ng/ml.

17. The method according to claim 16, wherein the stable pharmaceutical mucoadhesive gel composition is formulated for being maintained at the site of application for at least 4 to at least 12 hours.

18. The applicator according to claim 11, wherein the applicator contains less than 1.5 grams of the stable pharmaceutical mucoadhesive gel composition.

19. The stable pharmaceutical mucoadhesive gel composition of claim 1, in unit dose form, wherein a unit dosage of the stable pharmaceutical mucoadhesive gel composition comprises 40 up to 225 mg of the micronized progesterone.

* * * * *